(12) United States Patent
Dietrich et al.

(10) Patent No.: US 6,284,730 B1
(45) Date of Patent: Sep. 4, 2001

(54) METHODS USEFUL IN THE TREATMENT OF BONE RESORPTION DISEASES

(75) Inventors: John Dietrich, Etobicoke (CA); Sverker Ljunghall, Uppsala; Sven Sjögren, Billdal, both of (SE)

(73) Assignee: NPS Allelix Corp., Mississauga (CA)

( * ) Notice: Subject to any disclaimer, the term of this patent is extended or adjusted under 35 U.S.C. 154(b) by 0 days.

(21) Appl. No.: 09/125,247

(22) PCT Filed: Jun. 8, 1998

(86) PCT No.: PCT/SE98/01095

§ 371 Date: Aug. 14, 1998

§ 102(e) Date: Aug. 14, 1998

(87) PCT Pub. No.: WO98/57656

PCT Pub. Date: Dec. 23, 1998

(30) Foreign Application Priority Data

Jun. 19, 1997 (SE) .................................................. 9702401

(51) Int. Cl.⁷ ............................ A61K 38/16; A61K 38/00
(52) U.S. Cl. .................. 514/12; 514/8; 514/102; 514/107; 514/108
(58) Field of Search .................. 514/12, 8, 102, 514/107, 108

(56) References Cited

U.S. PATENT DOCUMENTS

| 4,698,328 | 10/1987 | Neer et al. . | |
|---|---|---|---|
| 4,822,609 | * 4/1989 | Flora | ............................ 514/12 |
| 5,118,667 | * 6/1992 | Adams et al. | .................... 514/12 |
| 5,510,370 | 4/1996 | Hock . | |

FOREIGN PATENT DOCUMENTS

| 0792639 A1 | * 3/1997 | (EP) . |
|---|---|---|
| WO 89/04173 | 5/1989 | (WO) . |
| WO 92/09304 | 6/1992 | (WO) . |
| WO 93/11786 | 6/1993 | (WO) . |
| WO 96/7416A1 | 3/1996 | (WO) . |
| 9607417A1 | * 3/1996 | (WO) . |

* cited by examiner

*Primary Examiner*—Frederick Krass
(74) *Attorney, Agent, or Firm*—Foley & Lardner

(57) ABSTRACT

The invention relates to a combined pharmaceutical preparation comprising parathyroid hormone and a bone resorption inhibitor, said preparation being adapted for (a) the administration of parathyroid hormone during a period of approximately 6 to 24 months; (b) after the administration of parathyroid hormone has been terminated, the administration of a bone resorption inhibitor during a period of approximately 12 to 36 months.

29 Claims, No Drawings

METHODS USEFUL IN THE TREATMENT OF BONE RESORPTION DISEASES

This appln. is a 371 of PCT/SE98/01095, filed Jun. 8, 1998.

TECHNICAL FIELD

The present invention relates to a combined pharmaceutical preparation comprising parathyroid hormone and a bone resorption inhibitor, for sequential use in the treatment of bone-related diseases.

BACKGROUND ART

Bone Formation and Resorption

In the adult individual (males as well as females) bone is continuously subject to remodeling. This is a process where bone resorption is closely linked to bone formation, through the concerted action of the bone active cells, i.e. the bone forming osteoblasts and the bone resorbing osteoclasts. These cells together form what is called a basal multicellular (metabolic) unit, or BMU. The remodeling process starts with activation of the lining cells (the cells that cover the unmineralized bone). The lining cells resorb the unmineralized bone, then retract and leave room for the osteoclasts which resorb the old, mineralized bone and create an environment which attracts the osteoblast to the same site. The osteoblasts thereafter lay down the organic matrix, which subsequently is becoming mineralized to form new bone. The resulting bone mass is thus determined by the balance between resorption by osteoclasts and formation by osteoblasts.

Consequently, there is a close relationship between the actions of the two cell types which is referred to as "coupling"; bone resorption always precedes bone formation. The coupling phenomenon means that even when the intention is to produce a positive balance per cycle it is still necessary to start with bone resorption. Typically, a BMU cycle takes 3 to 6 months to complete.

The rate by which the basal metabolic (multicellular) units are being activated, the activation frequency, also plays a role. A high activation frequency increases the rate by which bone is being lost if there is a negative balance per remodeling cycle. When activation frequency is increased the space that is being occupied by remodeling, the remodeling space, is also increased. This will give a lowered bone mass, since a greater portion of the bone is subject to resorption as part of the remodeling process.

The above outlined sequence of events is well known in the art and has formed the basis for the understanding of metabolic bone diseases and possible ways for their treatments.

Osteoporosis is a disease which is characterized by a reduced amount of bone tissue, usually of normal composition, which has reduced strength due to a combination of low bone mass and impaired architecture, and therefore carries an increased risk of fractures. In terms of remodeling, osteoporosis is the result of negative bone balance per remodeling cycle, i.e. less bone is formed than is being resorbed. In a small proportion of patients it is possible to determine a specific disease as responsible for the loss of bone (e.g. malabsorption of calcium and hypersecretion of corticosteroid hormones) but in the majority of patients no such disorder is identified. Such patients are classified as having "primary" osteoporosis. Bone is lost with advancing age in both sexes, but in females there is generally an increased rate of loss during the first years after the menopause (hence the term "postmenopausal" osteoporosis).

Bone Resorption Inhibitors

A number of agents have been used for the prevention and treatment of bone loss and osteoporosis, e.g. estrogen, vitamin D and bisphosphonates, such as alendronate (for a review, see: Osteoporosis (Marcus, R., Feldman, D. and Kelsey, F., Eds.) Academic Press, San Diego, 1996). Such agents mainly act through inhibition of bone resorption. By reducing the resorbed amount in each remodeling cycle, while keeping the formation intact, it is possible to reduce the negative bone balance and retard bone loss. At the same time they reduce the activation frequency and since the remodeling space is reduced there is only a limited increase of bone mass.

Most studies with bisphosphonates indicate that they increase bone mineral density of the lumbar spine in the actively treated patients with around 1 to 5%, depending on dose and type of bisphosphonate, during the first year of treatment, when compared with control patients given placebo. Both patients and controls generally receive calcium supplementation to ensure adequate calcium nutrition.

The antiresorptive agents can retard bone loss but, by definition, they do not increase bone mass within each remodeling unit. Many patients with fractures have severe bone loss at the time they come to clinical attention. Inhibition of bone resorption might not be enough to prevent fracture recurrences. Therefore it is urgent to develop therapies that can increase bone mass, i.e. anabolic agents.

Parathyroid Hormone

Parathyroid hormone (PTH) is an 84 amino acid polypeptide which is normally secreted from the parathyroid glands. PTH has an important physiological role to maintain serum calcium within a narrow range. Furthermore, it has anabolic properties when given intermittently. This has been well documented in a number of animal and open clinical studies, recently reviewed by Dempster, D. W. et al. (Endocrine Reviews 1993, vol. 14, 690–709). PFH has a multitude of effects on bone. Part of it is through the remodeling cycle. PTH causes both increased activation frequency and a positive balance per cycle.

Human PTH may be obtained through peptide synthesis or from genetically engineered yeast, bacterial or mammalian cell hosts. Synthetic human PTH is commercially available from Bachem Inc., Bubendorf, Switzerland. Production of recombinant human parathyroid hormone is disclosed in e.g. EP-B-0383751.

PTH when given alone, to a patient with osteoporosis, will stimulate bone formation within each remodeling cycle and cause a positive bone balance within each cycle. At the same time the number of remodeling units will greatly increase, i.e. the activation frequency is enhanced. These two mechanisms act in different directions on bone mass.

During therapy with PTH it has been calculated that the activation frequency is doubled. Although this will mean that the remodeling space is increased, bone mass (or bone density) is increased in trabecular bone. Thus bone mineral density is increased by 5 to 10% per year in the lumbar spine and is largely unaffected in the femoral neck, which contains a higher proportion of cortical bone. These two sites are where the most common and clinically important fractures occur in the population, both in males and females.

The presently known methods for treatment of osteoporosis utilize bone resorption inhibition of the BMU cycle, but have the drawbacks that their onset of effect is slow and limited, and that they only cause moderate increases of bone mineral density (bone mass) and may therefore be insufficient for the treatment of patients with osteoporosis in a stage where there is high risk of recurrent fractures.

Furthermore, it has not been shown that present methods can improve on the altered architecture that is a hallmark of advanced osteoporosis.

A method of treatment of bone metabolism disorders, utilizing the order of events in the BMU cycle, and comprising administering a bone active phosphonate and, sequentially, parathyroid hormone, is disclosed in WO 96/07417 (The Procter & Gamble Company). In that method, the bone active phosphonate is given for a period of greater than about 6 months, in various dosage regimens, but always prior to PTH.

Hodsman, A. et al. (J. Bone and Mineral Research, Vol. 10, Suppl. 1, abstract No. P288, p. S200, 1995) discloses a clinical trial involving treatment with PTH for 28 days, with or without sequential calcitonin for 42 days, with this cycle repeated at 3 months intervals for 2 years. Patients were then crossed over to clodronate, 28 days per 3 months, for one year. However, there was no beneficial effect in bone density from this sequential PTH/bisphosphonate treatment regimen.

WO 97/31640 (publication date Sep. 4, 1997) discloses a pharmaceutical composition comprising (a) an estrogen agonist/antagonist; and (b) a bone activating compound, such as parathyroid hormone. However, the periods of treatment are broadly defined and it is stated that the said compounds can be administered for periods from about three months to about three years.

DISCLOSURE OF THE INVENTION

Different combinations are conceivable for treating osteoporosis with resorption inhibitors and anabolic agents. The starting point for treatment, i.e. when the patient comes to the attention of the clinic, is a decreasing BMD (bone mineral density), due to the net formation rate being below the net resorption rate. Initial administration of a resorption inhibitor will reduce resorption rate by reducing the remodeling space and the activation frequency. Subsequent administration of an anabolic agent will then increase activation frequency and create an increased remodeling space. This coupling between resorption and reformation allows the formation rate to increase above the resorption rate and lead to increases in BMD. The resorption activity is a prerequisite for subsequent bone formation within the BMU.

However, it has surprisingly been found that when the anabolic agent was administered initially, ie. as the starting point, and is then followed by administration of the resorption inhibitor, the total increase in BMD is not only maintained but also much further increased. It appears that the initial increase in activation frequency by the anabolic agent creates not only formation of new bone, but also a large remodeling space. Subsequent administration by the resorption inhibitor, inhibits further increases in the remodeling space, by decreasing the activation frequency. Upon closing, or diminishing, the existing remodeling space, BMD is then allowed to increase more than was achieved during treatment with the anabolic agent alone during the first period.

The present invention is thus based on the concept of remodeling. By overriding the resorptive phase of the BMU over several consecutive cycles, it fortifies the anabolic action of PTH. In addition, by prolonging the treatment over several BMU cycles, it takes advantage of the opposite influences on the activation frequency which is increased by PTH and later reduced by bisphosphonates.

As mentioned above, WO 96/07417 discloses a method of treatment of bone metabolism disorders, comprising administering a bone active phosphonate and, subsequently, parathyroid hormone. The bone active phosphonate was thus given prior to PTH. The order of treatment regimens provides principally different treatment responses. Slowing down the remodeling cycle with a resorption inhibitor would limit the maximum anabolic effect that can be obtained with PTH. On the other hand, if PTH is given first over several BMU cycles, not only will it enhance the BMU positive bone balance significantly, it will also increase activation frequency to such an extent that effects of subsequent antiresorptive therapy will be enhanced.

According to the present invention, a bisphosphonate is given after PTH treatment, in order not only to maintain bone mass on the higher level by its antiresorptive action, but also to increase BMD by filling in the increased remodeling space through the reduction of activation frequency.

A BMU cycle, involving activation, resorption, formation, typically takes 3 to 6 months to complete. The number of BMU cycles acting concurrently determines the remodeling space. In order to create an increased and sustained remodeling space, treatment with an agent that increases the activation frequency must be of sufficient duration, ie. it must cover several BMU cycles (e.g. 6 to 12 months). Only then can the full potential of the treatment, with regards to increases in BMD, develop.

It has thus surprisingly been found that the method of treatment according to the invention achieves the advantageous result that bone mass is first rapidly increased during PTH treatment and thereafter further bone mineral density is gained, compared to the results achieved with bisphosphonates alone without prior activation by PTH. These findings are in contrast to previous studies in humans.

Consequently, the present invention provides in a first aspect a combined pharmaceutical preparation comprising parathyroid hormone and a bone resorption inhibitor, said preparation being adapted for (a) the administration of parathyroid hormone during a period of approximately 6 to 24 months, preferably about 12 (or above 12) months to 24 months or about 12 (or above 12) months to 18 months, or more preferably about 18 months; and (b) after the administration of said parathyroid hormone has been terminated, the administration of a bone resorption inhibitor during a period of approximately 6 to 36 months, preferably about 12 to 36 months or about 12 to 18 months, or more preferably about 12 months.

This sequence of treatments can be repeated at intervals of one to five years, until BMD has reached a value corresponding to "young normal mean". Preferably, the interval between treatments coincides with the period of one treatment cycle, i.e. 12 to 60 months, preferably 24 to 60 months or 24 to 42 months, or more preferably 30 to 36 months.

The term "parathyroid hormone" (PTH) encompasses naturally occurring human PTH, as well as synthetic or recombinant PTH (rPTH).

Further, the term "parathyroid hormone" encompasses full-length PTH(1-84) as well as PTH fragments. It will thus be understood that fragments of PTH variants, in amounts giving equivalent biological activity to PTH(1-84), can be incorporated in the formulations according to the invention, if desired. Fragments of PTH incorporate at least the amino acid residues of PTH necessary for a biological activity similar to that of intact PTH. Examples of such fragments are PTH(1-31), PTH(1-34), PTH(1-36), PTH(1-37), PTH(1-38), PTH(1-41), PTH(28-48) and PTH(25-39).

The term "parathyroid hormone" also encompasses variants and functional analogues of PTH. The present invention thus includes pharmaceutical formulations comprising such PTH variants and functional analogues, carrying modifications like substitutions, deletions, insertions, inversions or cyclisations, but nevertheless having substantially the biological activities of parathyroid hormone. Stability-enhanced variants of PTH are known in the art from e.g. WO 92/11286 and WO 93/20203. Variants of PTH can e.g. incorporate amino acid substitutions that improve PTH stability and half-life, such as the replacement of methionine residues at positions 8 and/or 18, and replacement of asparagine at position 16. Cyclized PTH analogues are disclosed in e.g. WO 98/05683.

Consequently, the invention includes a preparation as described above wherein the said parathyroid hormone is selected from the group consisting of:
  (a) full-length parathyroid hormone;
  (b) biologically active variants of full-length parathyroid hormone;
  (c) biologically active parathyroid hormone fragments; and
  (d) biologically active variants of parathyroid hormone fragments.

In this context, the term "biologically active" should be understood as eliciting a sufficient response in a bioassay for PTH activity, such as the rat osteosarcoma cell-based assay for PTH-stimulated adenylate cyclase production (see Rodan et al. (1983) J. Clin. Invest. 72, 1511; and Rabbani et al. (1988) Endocrinol. 123, 2709).

The PTH to be used in the pharmaceutical preparation according to the invention is preferably recombinant human PTH, such as full-length recombinant human PTH. Parathyroid hormone can be subcutaneously administered in an amount of approximately 0.1 to 5 µg/kg body weight, preferably 0.5 to 3 µg/kg, or more preferably 1 to 2.5 µg/kg body weight. Orally, nasally or pulmonary, PTH can be administered in an amount of 0.1 µg to 15 mg/kg.

The said bone resorption inhibitor can be a bisphosphonate, e.g. alendronate; or a substance with estrogen-like effect, e.g. estrogen; or a selective estrogen receptor modulator, e.g. raloxifene, tamoxifene, droloxifene, toremifene, idoxifene, or levormeloxifene; or a calcitonin-like substance, e.g. calcitonin; or a vitamin D analog; or a calcium salt.

The said bone resorption inhibitor is preferably administered in an amount of 0.05 to 500 mg, preferably around 10 mg.

In a further aspect, the invention provides the use of parathyroid hormone in combination with a bone resorption inhibitor in the manufacture of a medicament for the treatment or prevention of bone-related diseases, in particular osteoporosis, said medicament being adapted for (a) the administration of parathyroid hormone during a period of approximately 6 to 24 months; (b) after the administration of parathyroid hormone has been terminated, the administration of a bone resorption inhibitor during a period of approximately 12 to 36 months. The parathyroid hormone and the bone resorption inhibitor are as defined above.

In yet a further aspect, the invention provides a method of treatment or prevention of bone-related diseases, in particular osteoporosis, which comprises administering to a mammal, including man, in need of such treatment an effective amount of a pharmaceutical preparation as defined in the above. Consequently, such a method comprises administering to a mammal, including man, in need of such treatment (a) an effective amount of parathyroid hormone during a period of approximately 6 to 24 months; and (b) after the administration of parathyroid hormone has been terminated, an effective amount of a bone resorption inhibitor during a period of approximately 12 to 36 months.

The invention also includes a method of treatment or prevention of bone-related diseases which comprises administering, to a patient who has already been subject to treatment with parathyroid hormone during a period of approximately 6 to 24 months, after the administration of parathyroid hormone has been terminated, an effective amount of a bone resorption inhibitor during a period of approximately 12 to 36 months.

EXAMPLE OF THE INVENTION

Postmenopausal females (n=172) with osteoporosis were given intact human PTH (1-84), as a subcutaneous injection, for one year in doses from 50 to 100 micrograms daily. It was shown that bone mineral density of the spine was increased in the lumbar spine, on the average by 8%. Increases in individual patients were considerably more than 10%. The changes of the femoral neck were smaller and ranged from 1 to 3%.

When administration of PTH was interrupted, some patients (approximately 60) were given the bisphosphonate alendronate in a standard dose of 10 mg for one year. After the combined treatment, bone mineral density was further increased in that group of patients. The average gain in the femoral neck over the two years was 6% and of the lumbar spine 15%. Again, some individual responses were considerably larger and amounted to more than 25% in the spine.

These new observations demonstrate that it is possible to achieve an enhanced effect on bone mineral density with the sequential administration of PTH and bisphosphonates.

What is claimed is:

1. A method useful in the treatment of bone resorption diseases comprising administering to a mammal in need of such treatment or at increased risk to suffer from such disease:
  (a) an effective amount of parathyroid hormone during a period of approximately 6 to 24 months; and
  (b) after the administration of parathyroid hormone has been terminated, an effective amount of a bone resorption inhibitor during a period of approximately 6 to 36 months.

2. The method according to claim 1, adapted for said administration of parathyroid hormone for approximately 12 to 24 months.

3. The method according to claim 2, adapted for said administration of parathyroid hormone for approximately 18 months.

4. The method according to any one of claims 1, 2, or 3, adapted for said administration of bone resorption inhibitor for approximately 12 to 36 months.

5. The method according to claim 4, adapted for said administration of bone resorption inhibitor for approximately 12 to 18 months.

6. The method according to claim 5, adapted for said administration of bone resorption inhibitor for approximately 12 months.

7. The method according to any one of claims 1, 2, or 3, wherein said parathyroid hormone is selected from the group consisting of:
  (a) full-length parathyroid hormone;
  (b) biologically active variants of full-length parathyroid hormone;
  (c) biologically active parathyroid hormone fragments; and
  (d) biologically active variants of parathyroid hormone fragments.

8. The method according to any one of claims 1, 2, or 3, wherein the bone resorption inhibitor is selected from the group consisting of a biphosphonate, a selective estrogen receptor modulator, calcitonin, a vitamin D analog, and a calcium salt.

9. The method according to any one of claims 1, 2, or 3 for the treatment of osteoporosis.

10. The method of claim 4, wherein the parathyroid hormone is selected from the group consisting of:
   (a) full-length parathyroid hormone;
   (b) biologically active variants of full-length parathyroid hormone;
   (c) biologically active parathyroid hormone fragments; and
   (d) biologically active variants of parathyroid hormone fragments.

11. The method of claim 5, wherein the parathyroid hormone is selected from the group consisting of:
   (a) full-length parathyroid hormone;
   (b) biologically active variants of full-length parathyroid hormone;
   (c) biologically active parathyroid hormone fragments; and
   (d) biologically active variants of parathyroid hormone fragments.

12. The method of claim 6, wherein the parathyroid hormone is selected from the group consisting of:
   (a) full-length parathyroid hormone;
   (b) biologically active variants of full-length parathyroid hormone;
   (c) biologically active parathyroid hormone fragments; and
   (d) biologically active variants of parathyroid hormone fragments.

13. The method of claim 4, wherein the bone resorption inhibitor is selected from the group consisting of a biphosphonate, estrogen, a selective estrogen receptor modulator, calcitonin, a vitamin D analog, and a calcium salt.

14. The method of claim 5, wherein the bone resorption inhibitor is selected from the group consisting of a biphosphonate, estrogen, a selective estrogen receptor modulator, calcitonin, a vitamin D analog, and a calcium salt.

15. The method of claim 6, wherein the bone resorption inhibitor is selected from the group consisting of a biphosphonate, estrogen, a selective estrogen receptor modulator, calcitonin, a vitamin D analog, and a calcium salt.

16. The method of any one of claims 1, 2, or 3, wherein the bone resorption inhibitor is selected from the group consisting of alendronate, estrogen, raloxifene, tamoxifene, droloxifene, toremifene, idoxifene, levormeloxifene, and calcitonin.

17. The method of claim 4, wherein the bone resorption inhibitor is selected from the group consisting of alendronate, estrogen, raloxifene, tamoxifene, droloxifene, toremifene, idoxifene, levormeloxifene, and calcitonin.

18. The method of claim 5, wherein the bone resorption inhibitor is selected from the group consisting of alendronate, estrogen, raloxifene, tamoxifene, droloxifene, toremifene, idoxifene, levormeloxifene, and calcitonin.

19. The method of claim 6, wherein the bone resorption inhibitor is selected from the group consisting of alendronate, estrogen, raloxifene, tamoxifene, droloxifene, toremifene, idoxifene, levormeloxifene, and calcitonin.

20. The method of claim 4 for the treatment of osteoporosis.

21. The method of claim 5 for the treatment of osteoporosis.

22. The method of claim 6 for the treatment of osteoporosis.

23. The method of claim 7 for the treatment of osteoporosis.

24. The method of claim 8 for the treatment of osteoporosis.

25. The method of any one of claims 1, 2, or 3, wherein the mammal is a human.

26. The method of claim 6, wherein the mammal is a human.

27. The method of claim 7, wherein the mammal is a human.

28. The method of claim 8, wherein the mammal is a human.

29. The method of claim 9, wherein the mammal is a human.

* * * * *